United States Patent [19]

Scopes et al.

[11] Patent Number: 5,109,008
[45] Date of Patent: Apr. 28, 1992

[54] PHARMACEUTICALLY USEFUL FURO[3,2-C]PYRIDINES

[75] Inventors: David I. C. Scopes, Furneux Pelham; Duncan B. Judd, Ware; David J. Belton, Stevenage, all of England

[73] Assignee: Glaxo Group Limited, London, England

[21] Appl. No.: 423,202

[22] Filed: Oct. 18, 1989

[30] Foreign Application Priority Data

Oct. 18, 1988 [GB] United Kingdom ................ 8824400

[51] Int. Cl.$^5$ ..................... A61K 00/00; C07D 471/02
[52] U.S. Cl. ................................... 514/302; 546/114; 546/115; 546/116
[58] Field of Search ................. 546/114, 115, 116; 514/301, 302

[56] References Cited

U.S. PATENT DOCUMENTS

| | | | |
|---|---|---|---|
| 3,845,065 | 10/1974 | Shen et al. | 546/114 |
| 3,903,095 | 9/1975 | Shen et al. | 546/114 |
| 4,051,141 | 9/1977 | Castaigne | 546/114 |
| 4,210,649 | 7/1980 | Blanchard et al. | 514/301 |
| 4,335,128 | 5/1982 | Blanchard et al. | 514/301 |
| 4,579,863 | 4/1986 | Horwell et al. | 514/422 |
| 4,731,368 | 3/1988 | Hoffman, Jr. et al. | 546/114 |
| 4,999,359 | 3/1991 | Vecchietti et al. | 546/114 |

FOREIGN PATENT DOCUMENTS

| | | |
|---|---|---|
| 86/66824 | 12/1986 | Australia . |
| 0176309 | 4/1986 | European Pat. Off. . |
| 0228246 | 7/1987 | European Pat. Off. . |
| 0232989 | 8/1987 | European Pat. Off. . |
| 0233793 | 8/1987 | European Pat. Off. . |
| 0260041 | 3/1988 | European Pat. Off. . |
| 0271273 | 6/1988 | European Pat. Off. . |
| 0275696 | 7/1988 | European Pat. Off. . |
| 0330360 | 8/1989 | European Pat. Off. . |
| 333427 | 9/1989 | European Pat. Off. . |
| 1445524 | 8/1976 | United Kingdom . |

Primary Examiner—Bernard Dentz
Attorney, Agent, or Firm—Bacon & Thomas

[57] ABSTRACT

Compounds are disclosed of formula (I)

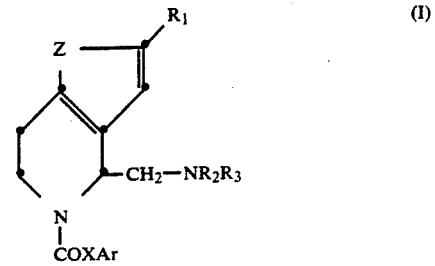

wherein
$R_1$ represents hydrogen, unsubstituted or substituted $C_{1-6}$alkyl, halogen, $-COR_4$ or $-CO_2R_4$ (where $R_4$ represents hydrogen or unsubstituted or substituted $C_{1-6}$alkyl);
$R_2$ and $R_3$ are the same or different and are $C_{1-6}$alkyl or $C_{3-6}$alkenyl; or $-NR_2R_3$ forms a 5-membered (optionally containing an oxygen atom adjacent to the nitrogen) or a 6-membered ring, which ring optionally contains one unit of unsaturation and which is unsubstituted or substituted by hydroxy, $C_{1-6}$acyloxy, oxo, optionally substituted methylidene, $-COR_5$ (where $R_5$ represents $C_{1-6}$alkyl, $OR_6$ or $-NHR_6$, and
$R_6$ represents hydrogen, $C_{1-6}$alkyl, aryl or ar($C_{1-6}$)alkyl) or said ring is substituted by $=NOR_7$ (where $R_7$ represents $C_{1-6}$alkyl);
Z represents $-O-$ or $-S-$;
X represents a direct bond, $-CH_2-$ or $-CH_2O-$;
Ar represents a substituted phenyl moiety;
and pharmaceutically acceptable salts thereof.

The compounds are indicated as useful in the treatment of pain and cerebral ischaemia.

Processes and intermediates for their preparation and pharmaceutical compositions containing them are also disclosed.

19 Claims, No Drawings

PHARMACEUTICALLY USEFUL FURO[3,2-C]PYRIDINES

This invention relates to heterocyclic compounds, to processes for their preparation, to pharmaceutical compositions containing them and to their medical use. In particular, the invention relates to compounds which act as agonists at kappa opioid receptors.

Compounds which are kappa opioid receptor agonists have been indicated in the art for the treatment of a number of conditions and have been described, for example, as analgesics, as diuretics and in the treatment of cerebral ischaemia. Opioid analgesia is generally thought to be mediated by either mu or kappa receptors in the brain (see, for example, Tyers M. B., *Br. J. Pharmacol*, (1980), 69, 503-512). Most existing clinically used opioid analgesics such as morphine and codeine act as mu-receptor agonists. However, these compounds have undesirable and potentially dangerous dependence forming side effects. There is thus a need for a strong analgesic with low dependence liability and a compound which is a selective kappa-receptor agonist would fulfil such a role.

Cerebral ischaemia or lack of blood flow in the brain, may result from a number of conditions, including, for example, stroke, head injuries or brain tumour. The resulting lack of oxygen to the brain cells causes neuronal damage and depending on the region of the brain involved, death or permanent disability may occur.

A number of classes of compounds which act as agonists at kappa opioid receptors have been described in the art.

N-(2-Aminocyclohexyl)benzeneacetamide derivatives having kappa receptor agonist activity of use in the treatment of cerebral ischaemia are disclosed in published European Patent Application No. 176309. Substituted trans-1,2-diaminocyclohexyl amide compounds having selective kappa opioid receptor binding activity are disclosed in U.S. Pat. No. 4,579,863. These compounds are described as being useful as analgesic, diuretic and psychotherapeutic agents.

European Patent Application No. 233793 discloses certain decahydroquinoline derivatives which act at kappa opioid receptors having anti-arrhythmic, anti-ischaemic and hypotensive activity.

Piperidine and tetrahydroisoquinoline derivatives having kappa receptor agonist activity of use in the treatment of pain are disclosed in published Australian Patent Application No. 86/66824 and also in published European Patent Application Nos. 232989, 228246, 260041 and 275696.

Furo- and thieno-pyridine derivatives useful in the treatment of elevated ocular pressure are disclosed in European Patent Application No. 271273 and U.S. Pat. No. 4,731,368. Other furo- and thieno-pyridine derivatives are disclosed in U.S. Pat. Nos. 4,210,649, 4,335,128, 3,903,095 and 3,845,065 and UK Patent Specification No. 1445524. These compounds are described as being useful inter alia as antiinflammatory, vasodilator, blood-platelet aggregation inhibitors, tranquilisers, antipyretic and analgesic agents. There is no suggestion that these compounds have kappa receptor agonist activity.

We have now found a novel group of furo- and thieno-pyridine derivatives which are selective kappa opioid receptor agonists. These compounds are therefore of interest in the treatment of conditions where the underlying aetiology indicates that treatment with a kappa opioid receptor agonist would be beneficial.

Thus, the present invention provides compounds of formula (I):

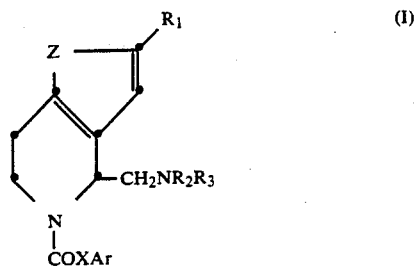

wherein
$R_1$ represents hydrogen, unsubstituted or substituted $C_{1-6}$ alkyl, halogen, —$COR_4$ or —$CO_2R_4$ (where $R_4$ represents hydrogen or unsubstituted or substituted $C_{1-6}$ alkyl);
$R_2$ and $R_3$ are the same or different and are $C_{1-6}$ alkyl or $C_{3-6}$ alkenyl; or —$NR_2R_3$ forms a 5-membered (optionally containing an oxygen atom adjacent to the nitrogen) or a 6-membered ring, which ring optionally contains one unit of unsaturation and which is unsubstituted or substituted by hydroxy, $C_{1-6}$ acyloxy, oxo, optionally substituted methylidene, —$COR_5$ (where $R_5$ represents $C_{1-6}$ alkyl, $OR_6$ or —$NHR_6$, and $R_6$ represents hydrogen, $C_{1-6}$ alkyl, aryl or ar($C_{1-6}$)alkyl) or said ring is substituted =$NOR_7$ (where $R_7$ represents $C_{1-6}$alkyl);
Z represents —O— or —S—;
X represents a direct bond, —$CH_2$— or —$CH_2O$—;
Ar represents a substituted phenyl moiety;
and pharmaceutically acceptable salts thereof.

As used herein, a substituted or unsubstituted $C_{1-6}$ alkyl group or the alkyl moiety of an ar($C_{1-6}$)alkyl group may be straight or branched chain and is conveniently $C_{1-4}$ alkyl, for example methyl. Where $R_1$ represents a substituted alkyl group, suitable substituents include for example hydroxy.

A halogen substituent in the compounds of formula (I) may be a fluorine, chlorine, bromine or iodine atom.

An alkenyl group may be a straight or branched chain group containing one or more units of unsaturation, which units of unsaturation may be conjugated or unconjugated. Where $R_2$ and/or $R_3$ in the compounds of formula (I) represents an alkenyl group, it will be appreciated that no double bond will be attached to the carbon atom adjacent to the nitrogen.

The term 'optionally substituted methylidene' as used herein includes methylidene substituted by any substituent conventional in the art. In the compounds of formula (I), the methylidene group may conveniently be substituted to form a conjugated system. Suitable substituents which form a conjugated system with the methylidene double bond include, for example, nitrile, phenyl, carboxyl and amido. Alternatively the methylidene group may conveniently be substituted by, for example, by a $C_{1-6}$ alkyl group, an ar($C_{1-6}$)alkyl group such as phenethyl a $C_{1-6}$ hydroxyalkyl group such as hydroxymethyl, a $C_{1-6}$ carboxyalkyl group such as methoxycarbonylethyl or $C_{1-6}$ amidoalkyl group such as aminocarbonylethyl.

Where —$NR_2R_3$ forms a substituted or unsubstituted 5 or 6-membered ring optionally containing one unit of unsaturation this may be, for example, a substituted or unsubstituted pyrrolidine, isoxazolidine or tetrahydropyridine ring. It will be appreciated that where the ring formed by —NR$_2$R$_3$ contains a unit of unsaturation, this will not be attached to a carbon atom adjacent to the nitrogen atom.

The term 'a substituted phenyl moiety' as used herein is a phenyl moiety substituted by one or more conventional substituents in the art, which substituents may form a second ring optionally containing one or more units of unsaturation. In the compounds of formula (I), Ar conveniently represents a phenyl moiety which is substituted by one or more C$_{1-6}$ alkyl groups or electron-withdrawing substituents, or in which two adjacent substituents form a second ring. Suitable electron-withdrawing substituents include, for example, halogen (for example, fluorine, chlorine or bromine), —CF$_3$ or —NO$_2$. Where two substituents on the phenyl ring form a second ring, Ar may suitably represent naphthyl, for example 1-naphthyl or 2-naphthyl. Ar is preferably phenyl substituted at the meta and/or para positions on the phenyl ring by one or more halogens, for example chlorine and is typically a 3,4-dichlorophenyl moiety.

Conveniently R$_1$ may be, for example, a hydrogen atom or a group —CHO, —CH$_2$OH or —CH$_3$.

R$_2$ and R$_3$ may each independently represent a C$_{1-6}$ alkyl group such as methyl, or —NR$_2$R$_3$ may suitably represent a pyrrolidine or tetrahydropyridine ring which may be optionally substituted, for example, by =O or more preferably by —OH.

—NR$_2$R$_3$ preferably represents a substituted or unsubstituted tetrahydropyridine ring or more preferably a substituted or unsubstituted pyrrolidine ring. Where —NR$_2$R$_3$ represents a substituted ring, the substituent in this ring is preferably attached to the carbon atom $\beta$ to the nitrogen atom. Where the substituent is an acetoxy or hydroxy group it is preferably in the S configuration.

X preferably represents —CH$_2$—.

In one preferred class of compounds of formula (I), Z represents —O—.

R$_1$ preferably represents a hydrogen atom or a methyl group.

In another preferred class of compounds of formula (I) NR$_2$R$_3$ represents a pyrrolidine ring which is unsubstituted or substituted by =O or —OH.

In an alternative preferred class of compounds of formula (I) NR$_2$R$_3$ represents a tetrahydropyridine ring.

In a further preferred class of compounds of formula (I) Ar represents a halosubstituted phenyl moiety in particular a chlorosubstituted phenyl moiety such as 3,4-dichlorophenyl.

In another preferred class of compounds of formula (I) Ar represents a naphthyl moiety.

A preferred group of compounds falling within the scope of formula (I) is that in which R$_1$ represents a hydrogen atom or a group —CHO or —CH$_2$OH; —NR$_2$R$_3$ forms an unsubstituted or more preferably a substituted pyrrolidine or tetrahydropyridine ring; X represents —CH$_2$—; Z represents —O—; Ar represents halosubstituted phenyl; and pharmaceutically acceptable salts thereof. Particularly preferred compounds falling within this class are those in which Ar represents chlorosubstitued phenyl.

Another preferred group of compounds falling within the scope of formula (I) is that in which R$_1$ represents a hydrogen atom or a methyl group; —NR$_2$R$_3$ forms a pyrrolidine ring substituted by =O or —OH; X represents —CH$_2$—; Z represents —O—; Ar represents halosubstituted phenyl; and pharmaceutically acceptable salts thereof. Particularly preferred compounds falling within this class are those in which Ar represents chlorosubstituted phenyl.

Preferred compounds according to the invention include:

5-[(3,4-Dichlorophenyl)acetyl]-4,5,6,7-tetrahydro-4-[(3-hydroxy-1-pyrrolidinyl)methyl]furo[3,2-c]pyridine;

5-[(3,4-Dichlorophenyl)acetyl]-4,5,6,7-tetrahydro-4-[(3-oxo-1-pyrrolidinyl)methyl]furo[3,2-c]pyridine;

5-[(3,4-Dichlorophenyl)acetyl]-4,5,6,7-tetrahydro-4-[(3-hydroxy-1-pyrrolidinyl)methyl]-2-methylfuro[3,2-c]pyridine;

4,5,6,7-Tetrahydro-4-[(3-hydroxy-1-pyrrolidinyl)methyl]-5-(1-naphthalenylacetyl)furo[3,2-c]pyridine;

5-[(4-Chlorophenoxy)acetyl]-4,5,6,7-tetrahydro-4-[(3-hydroxy-1-pyrrolidinyl)methyl]furo[3,2-c]pyridine;

5-[(3,4-Dichlorophenyl)acetyl]-4,5,6,7-tetrahydro-4-[(1,2,3,6-tetrahydro-1-pyridinyl)methyl]furo[3,2-c]pyridine;

and pharmaceutically acceptable salts thereof.

A particularly preferred compound according to the invention is: [S-(R*R*)]-(—)5-](3,4-Dichlorophenyl)acetyl]-4,5,6,7-tetrahydro-4](3-hydroxy-1-pyrrolidinyl)methyl]furo[3,2-c]pyridine, which has the following formula:

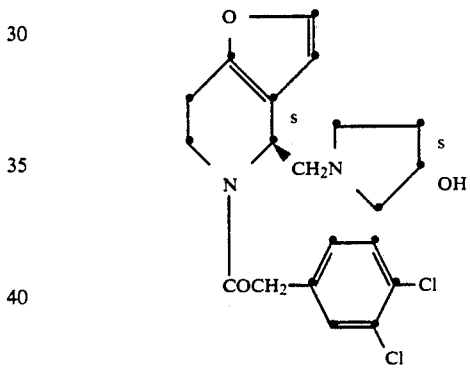

and its pharmaceutically acceptable salts.

Compounds of formula (I) contain at least one chiral centre and may exist in more than one stereoisomeric form. The invention includes within its scope all enantiomers, diastereomers and mixtures thereof.

It is believed that the activity of compounds falling within the scope of formula (I) resides primarily in the stereoisomeric form represented by formula (Ia)

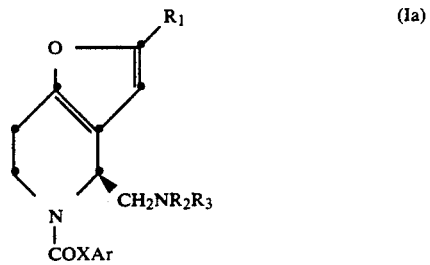

In a particularly preferred aspect the invention therefore provides compounds of formula (I) as described above having the stereoisomeric form represented by formula (Ia).

The invention also embraces all geometric isomers of compounds of formula (I).

Suitable pharmaceutically acceptable salts are those conventionally known in the art. Examples of pharmaceutically acceptable salts include acid addition salts formed with inorganic acids, such as hydrochlorides, hydrobromides, phosphates and sulphates, and with organic acids, for example tartrates, maleates, furmarates, succinates and sulphonates. Other salts which are not pharmaceutically acceptable may be useful in the preparation of compounds of formula (I) and these form a further part of the invention.

Compounds of the invention may readily be isolated in association with solvent molecules by crystallisation from or evaporation of an appropriate solvent. It is intended to include such solvates within the scope of the invention.

Compounds of the invention may readily be isolated in association with solvent molecules by crystallisation from or evaporation of an appropriate solvent. It is intended to include such solvates within the scope of the invention.

The kappa receptor activity of the compounds of the invention has been demonstrated in vitro in the field stimulated rabbit vas deferens preparation using the procedure described by A. G. Hayes and A. Kelly, *Eur. J. Pharmacol*, 110, 327–372 (1985). In addition compounds falling within formula (I) have been shown to have analgesic activity using standard laboratory animal tests such as the mouse acetylcholine abdominal constriction test (M. B. Tyers, *Brit. J. Pharmacol*, 1980, 69, 503–512). Compounds of the invention and their pharmaceutically acceptable salts thus possess analgesic activity with the potential for low dependence liability and are therefore useful in the relief of pain.

Compounds of the invention are also of value in protecting against neuronal damage resulting from cerebral ischaemia which may be demonstrated for example in the standard laboratory gerbil bilateral carotid occlusion model. Thus, compounds of the invention and their pharmaceutically acceptable salts are also useful in treating or relieving the effects of cerebral ischaemia.

Accordingly, the invention also provides a compound of formula (I) or a pharmaceutically acceptable salt thereof for use in medicine, in particular for the treatment of conditions where kappa receptor agonists are indicated, (for example as analgesics and in the treatment of cerebral ischaemia).

In an alternative or further aspect there is provided a method of treatment of a mammal, including man, comprising administration of an effective amount of a compound of formula (I) or a pharmaceutically acceptable salt thereof in particular in the treatment of conditions where the use of a kappa receptor agonist is indicated.

The invention also provides the use of a compound of formula (I) or a pharmaceutically acceptable salt thereof for the manufacture of a medicament for the treatment of conditions where kappa receptor agonists are indicated.

It will be appreciated that compounds of the invention will primarily be of use in the alleviation of established symptoms but prophylaxis is not excluded.

Compounds of formula (I) may be administered as the raw chemical but the active ingredient is preferably presented as a pharmaceutical formulation. The active ingredient may conveniently be presented in unit dose form.

Thus, according to another aspect, the invention provides a pharmaceutical composition comprising at least one compound of formula (I) or a pharmaceutically acceptable salt thereof and formulated for administration by any convenient route conventional in the art. Such compositions are preferably in a form adapted for use in medicine, in particular human medicine and can conveniently be formulated in conventional manner and normally using one or more pharmaceutically acceptable carriers or excipients. Compounds according to the invention may conveniently be formulated for oral or parenteral administration.

For oral administration, the pharmaceutical compositions may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compounds of the invention may be formulated for parenteral administration by injection conveniently intravenous or subcutaneous injection, for example by bolus injection or continuous intravenous infusion. Formulations for injection may be presented in unit dosage form, for example, in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed dose of the compounds of the invention for the relief of pain or the treatment of cerebral ischaemia is 0.01 to 100 mg/kg body weight, preferably 0.01 to 10 mg/kg body weight, most preferably 0.1 to 10 mg/kg body weight per day.

According to another aspect of the invention, compounds of formula (I) and physiologically acceptable salts thereof may be prepared by the general methods outlined below. In the following methods, $R_1$, $R_2$, $R_3$, X, Z and Ar are as defined for formula (I) unless otherwise indicated.

According to one general process (A) compounds of formula (I) may be prepared by reacting a compound of formula (II)

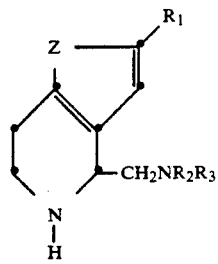

with a reagent serving to introduce the group —COXAr.

Thus, for example, compounds of formula (I) may be prepared by reacting a compound of formula (II) with an acid $ArXCO_2H$ or an acylating agent corresponding thereto or a salt thereof.

Suitable acylating agents corresponding to the acid $ArXCO_2H$ which may conveniently be used include, for example, acid halides (for example acid chlorides), alkyl esters (for example, methyl or ethyl esters) and mixed anhydrides. Such acylating agents may conveniently be prepared from the acid itself by conventional methods.

The reaction of a compound of formula (II) with an acid $ArXCO_2H$ is desirably effected in the presence of a coupling agent such as carbonyl diimidazole, dicyclohexylcarbodiimide or diphenylphosphoryl azide in a suitable reaction medium and conveniently at a temperature of from $-50°$ to $+50°$ C., preferably at room temperature. The reaction may be effected in a suitable reaction medium such as an ether (for example tetrahydrofuran), a haloalkane (for example, dichloromethane), a nitrile (for example acetonitrile), an amide (for example dimethylformamide), or mixtures thereof.

The reaction of a compound of formula (II) with an acylating agent corresponding to the acid $ArXCO_2H$ may conveniently be effected in a reaction medium and at a temperature in the range as described above and optionally in the presence of a base. Suitable bases which may be employed include, for example, organic bases such as pyridine or triethylamine or inorganic bases such as calcium carbonate or sodium bicarbonate.

Compounds of formula (II) are novel and form a further aspect of the invention.

Compounds of formula (II) may conveniently be prepared for example from compounds of formula (III)

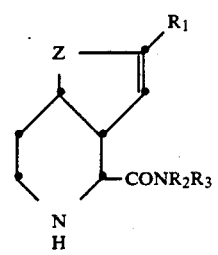

by reduction using a suitable reducing agent, for example a metal hydride such as lithium aluminium hydride in a solvent such as tetrahydrofuran.

Compounds of formula (III) may themselves be prepared for example from the corresponding carboxylic acid or an acylating agent corresponding thereto such as an alkyl ester (for example the methyl ester) by reaction with an amine $HNR_1R_3$ using conventional methods. The corresponding acid or ester may itself conveniently be prepared, for example, by cyclisation of the acid salts of known amines of formula (IV)

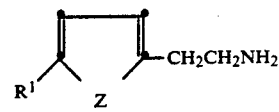

with an aldehyde, such as methyl glyoxylate.

According to another general process (B) a compound of formula (I) may be prepared by reductive amination of a compound of formula (V)

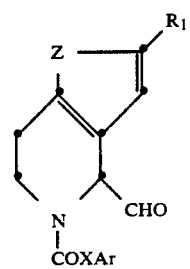

with an amine $R_3R_2NH$ in the presence of a suitable reducing agent.

The reduction may be effected using an alkali metal or alkaline earth metal borohydride or cyanoborohydride (for example sodium borohydride or cyanoborohydride) in a suitable solvent, for example an alcohol such as methanol and at a suitable temperature, conveniently room temperature. The reaction may optionally be performed in the presence of an acid such as acetic acid.

Alternatively, the reduction may be effected catalytically, for example, using hydrogen in the presence of a metal catalyst such as Raney nickel, platinum, platinum oxide, palladium or rhodium which may be supported, for example, on charcoal. The reaction may conveniently be carried out in a suitable solvent such as an alcohol (for example ethanol), an amide (for example dimethylformamide) an ether (for example tetrahydrofuran) at a suitable temperature such as ambient temperature and optionally in the presence of an acid catalyst.

Compounds of formula (V) may be prepared, for example, from compounds of formula (VI)

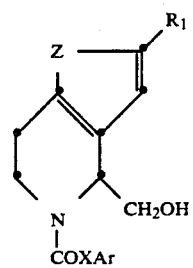

by oxidation using conventional methods for example using an oxidising agent such as an acid anhydride or acid chloride complex with dimethylsulphoxide (for example oxalylchloride-dimethylsulphoxide) in a solvent such as dichloromethane followed by treatment with a base such as triethylamine.

According to a further general process (C), a compound of formula (I) according to the invention may be converted into another compound of the invention using conventional procedures. It will be appreciated that where a compound of formula (I) contains an identical substituent at more than one position in the molecule, process (C) covers the conversion of either or both substituents to another substituent falling within formula (I).

According to one embodiment of process (C), a compound of formula (I) containing an oxo group may be converted into the corresponding optionally substituted methylidene derivative by reaction with an appropriate Wittig reagent, for example a phosphonate (such as trimethylphosphonate) or a phosphorane prepared by reacting an appropriate triarylphosphonium salt (such as methyltriphenylphosphonium) with a base. Suitable bases which may be used include, for example, alkali metal hydrides such as sodium hydride, alkali metal alkoxides such as sodium or potassium t-butoxide or alkali lithiums such as n-butyl lithium. The reaction may conveniently be carried out in a solvent such as an ether, for example tetrahydrofuran, and at a temperature of from $-70°$ to $+50°$.

Compounds of formula (I) containing a hydroxy substituent at one or more positions of the molecule can conveniently be prepared by reduction of the corresponding oxo compound using a suitable reducing agent such as an alkali metal borohydride or cyanoborohydride (for example sodium borohydride) or a metal hydride (for example diisobutyl aluminium hydride or lithium aluminium hydride) in a suitable solvent (for example, an alcohol such as ethanol or a hydrocarbon solvent such as toluene). Compounds of formula (I) containing an acyloxy group may be prepared from the corresponding hydroxy substituted compound using conventional acylation procedures.

Compounds of formula (I) containing one or more oxo groups may be prepared by oxidation of the corresponding alcohol using a suitable oxidising agent, for example an acid anhydride or acid chloride complex with dimethylsulphoxide (such as oxalylchloride-dimethylsulphoxide) in a solvent such as dichloromethane, conveniently at low temperature, followed by treatment with a base such as triethylamine.

Compounds of formula (I) in which $R_1$ represents a group —CHO may be prepared from the corresponding compound in which $R_1$ represents a hydrogen atom by conventional formylation procedures for example using phosphorylchloride and dimethylformamide.

Compounds of formula (I) containing an oxime substituent may conveniently be prepared from the corresponding oxo derivative by conventional oximation procedures, for example by reaction with an appropriate amine in a suitable solvent such as pyridine, conveniently at room temperature.

As well as being employed as the last main step in the reaction sequence, the general methods discussed above may also be used to introduce a desired group at any intermediate stage in the preparation of compounds of formula (I). It will be appreciated that the sequence of reactions will be chosen such that the reaction conditions do not affect groups present in the molecule which are required in the final product.

The general process described above may yield the product of the general formula (I) as an individual stereoisomer or as a mixture of stereoisomers. Diastereoisomers may be separated at any convenient point in the overall synthesis by conventional methods for example chromatography. Specific enantiomers may be obtained by resolution of a racemic mixture at any convenient point in the overall synthesis by the use of conventional methods, see for example "Stereochemistry of Carbon Compounds by E. L. Eliel" (McGraw Hill, 1962).

Where it is desired to isolate a compound of the invention as a salt, this may be formed by conventional methods, for example by treatment with an acid or base in a suitable solvent such as an ether (for example diethyl ether), a nitrile (for example acetonitrile), a ketone (for example acetone) a halogenated hydrocarbon (for example dichloromethane) or an ester (for example ethyl acetate). Salts may also be formed by conversion of one salt into another using conventional methods.

The invention is further illustrated by the following non-limiting examples.

All temperature are in °C. Chromatography was carried out in the conventional manner by flash column chromatography on silica (Merck 9385) and thin layer chromatography (t.l.c.) on silica except where otherwise stated. Solvents were dried with $Na_2SO_4$ unless otherwise indicated.

INTERMEDIATE 1

Methyl 4,5,6,7-tetrahydrofuro[3,2-c]pyridine-4-carboxylate

A solution of 2-furanethanamine (0.2 g) in dry diethyl ether (5 ml) was treated with ethereal hydrochloride. The resulting solid was dried in vacuo and dissolved in acetonitrile (10 ml). Freshly distilled methyl glyoxylate (0.2 g) was added and the mixture was stirred at ambient temperature for 3 h. The resulting precipitate was filtered off to give the title compound as a solid (0.14 g) m.p. 144°–145°.

EXAMPLE 1

5-[(3,4-Dichlorophenyl)acetyl]-4,5,6,7-tetrahydro-4-(1-pyrrolidinyl methyl)furo[3,2-c]pyridine i)

1-[(4,5,6,7-Tetrahydrofuro[3,2-c]pyridin-4-yl)carbonyl]pyrrolidine

A solution of Intermediate 1 (0.1 g) in dry pyrrolidine (0.2 ml) was heated at 120° C. in a sealed vessel for 1 h. The solvent was removed in vacuo and the residue (0.11 g) was purified by flash column chromatography eluting with dichloromethane/methanol/ammonia (200:8:1) to give the title compound as a solid (60 mg) m.p. 85°–86°.

(ii)

4,5,6,7-Tetrahydro-4-(1-pyrrolidinylmethyl)furo[3,2-c]pyridine

To a suspension of lithium alumimium hydride (0.2 g) in dry tetrahydrofuran (30 ml) was added a solution of the product of stage (i) (0.58 g) in tetrahydrofuran (10 ml) and the mixture was stirred at ambient temperature for 1 h. Water (0.2 ml), aqueous sodium hydroxide (2M; 0.6 ml) and water (0.2 ml) were cautiously added and the mixture was filtered. The filtrate was evaporated, the residue was dissolved in dichloromethane (20 ml), dried and evaporated in vacuo to give the title compound as an oil (0.54 g). T.l.c. $SiO_2$ dichloromethane/methanol/ammonia (75:10:2) Rf 0.5.

(iii)

5-[(3,4-Dichlorophenyl)acetyl]-4,5,6,7-tetrahydro-4-(1-pyrrolidinylmethyl)furo[3,2-c]pyridine A solution of 3,4-dichlorophenylacetic acid (0.73 g) in dry dichloromethane (10 ml) was treated with 1,1′-carbonyldiimidazole (0.56 g) and the solution was stirred at ambient temperature for 1 h. A solution of the product of stage (ii) (0.58 g) in dichloromethane (5 ml) was added and the mixture was stirred at ambient temperature for 20 h. The reaction mixture was washed with aqueous sodium carbonate (2M; 2×20 ml), dried and evaporated in vacuo to give an oily residue (1.2 g). The residue was purified by flash column chromatography eluting with dichloromethane/methanol/ammonia (200:8:1) to give the free base of the title compound as a gum (0.56 g). A solution of the gum (0.15 g) in ethyl acetate (10 ml) and was treated with a solution of fumaric acid (45 mg) in ethyl acetate (25 ml). The resulting solid was filtered off to give the title compound as a solid (0.14 g) m.p. 220°-221°.

T.l.c. (SiO$_2$) Dichloromethane/methanol/ammonia 150:8:1 Rf 0.4.

EXAMPLE 2

5-[(3,4-Dichlorophenyl)acetyl]-4,5,6,7-tetrahydro-4-[(3-hydroxy-1-pyrrolidinyl)methyl]furo[3,2c]pyridine hydrochloride (i)

1-[(4,5,6,7-Tetrahydrofuro[3,2-c]pyridin-4-yl)carbonyl]-3-pyrrolidinol

A mixture of Intermediate 1 (0.75 g) and 3-pyrrolidinol (1 ml) was heated in a sealed vessel at 120° for 1 h. Excess reagent was removed in vacuo and the residue was purified by flash column chromatography eluting with dichloromethane/methanol/ammonia (100:10:2) to give the title compound as a foam (0.655 g). T.l.c. SiO$_2$ dichloromethane/methanol/ammonia 75:10:2 Rf 0.5.

(ii)

1-[(4,5,6,7-Tetrahydrofuro[3,2-c]pyridin-4-yl)methyl]-3-pyrrolidinol

To a suspension of lithium aluminium hydride (0.22 g) in dry tetrahydrofuran (15 ml) was added a solution of the product of stage (i) (0.655 g) in dry tetrahydrofuran (25 ml) over a 15 min period at ambient temperature. The mixture was stirred at 40° for 1 h and then at ambient temperature for 2 h. Water (0.22 ml) was cautiously added, followed by aqueous sodium hydroxide solution (2M; 0.65 ml) and water (0.22 ml). The mixture was filtered and the filtrate was evaporated in vacuo, to give the title compound as an oil (0.6 g).

T.l.c. SiO$_2$ Dichloromethane/methanol/ammonia (75:10:2) Rf 0.2.

(iii)

5-[(3,4-Dichlorophenyl)acetyl]-4,5,6,7-tetrahydro-4-[(3-hydroxy-1-pyrrolidinyl)methyl]furo[3,2-c]pyridine hydrochloride A mixture of 3,4-dichlorophenylacetic acid (0.83 g) and 1,1′-carbonyldiimidazole (0.66 g) in dry dichloromethane (20 ml) was stirred for 1 h at ambient temperature. A solution of the product of stage (ii) (0.6 g) in dry dichloromethane (10 ml) was added and the mixture was stirred for 20 h at ambient temperature. The reaction mixture was poured into aqueous sodium carbonate solution (2M; 10 ml) and extracted with dichloromethane (2×20 ml). The organic solution was dried, and evaporated to give an oily residue. The residue was purified by flash column chromatography eluting with dichloromethane/methanol/ammonia (150:8:1) to give the free base of the title compound as an oil (0.30 g). A solution of the free base (0.08 g) in diethyl ether (10 ml) was treated with an ethereal solution of hydrogen chloride to give the title compound as a solid (0.048 g) m.p. 189°-90°.

T.l.c. SiO$_2$ dichloromethane/methanol/ammonia 150:8:1 Rf 0.2.

EXAMPLE 3

5-[(3,4-Dichlorophenyl)acetyl]-4,5,6,7-tetrahydro-4-(1-pyrrolidinylmethyl)furo[3,2-c]pyridine-2-carboxyaldehyde fumarate A mixture of dry dimethylformamide (0.12 ml) and phosphorylchloride (0.2 ml1) was stirred at 0°-5° for 10 min and a solution of the product of Example 1 (0.4 g) in dry dimethylformamide (0.4 ml) was added. The mixture was stirred at 0°-5° for 1 h and then at ambient temperature for 2 h. The reaction mixture was poured into aqueous sodium carbonate (2M; 25 ml) and the mixture was extracted with dichloromethane (2×25 ml). The organic extract was dried and evaporated to give an oily residue which was purified by flash column chromatography eluting with dichloromethane/methanol/ammonia (200:8:1) to give the free base of the title compound as a foam (0.38 g). A solution of the free base (40 mg) in ethyl acetate/methanol was treated with a solution of fumaric acid (15 mg) in ethyl acetate/methanol to give the title compound as a solid (28 mg) m.p. 207°.

T.l.c. SiO$_2$ dichloromethane/methanol/ammonia 150:8:1 Rf 0.35

EXAMPLE 4

5-[(3,4-Dichlorophenyl)acetyl]-4,5,6,7-tetrahydro-4-(1-pyrrolidinyl-methyl)furo[3,2-c]pyridine-2-methanol fumarate A solution of the product of Example 3 (0.2 g) in ethanol (3 ml) was treated with sodium borohydride (15 mg) and the mixture was stirred at ambient temperature for 4 h. Hydrochloric acid (2M; 0.5 ml) was cautiously added and the solvent was removed in vacuo. The residue was dissolved in dichloromethane (20 ml) and washed with aqueous sodium carbonate (2M; 10 ml). The organic solution was dried and evaporated to give an oily residue, which was purified by flash column chromatography eluting with dichloromethane/methanol/ammonia (150:8:1) to give the free base of the title compound as a foam (0.08 g). A solution of the free base in a mixture of ethyl acetate/methanol was treated with a solution of fumaric acid (20 mg) in a mixture of ethyl acetate and methanol to give the title compound as a solid (50 mg) m.p. 177° dec.

T.l.c. SiO$_2$ Dichloromethane/methanol/ammonia 150:8:1 Rf 0.35

EXAMPLE 5

5-[(3,4-Dichlorophenyl)acetyl]-4,5,6,7-tetrahydro-4-[(3-oxo-1-pyrrolidinyl)methyl]furo[3,2-c]pyridine fumarate A solution of oxalylchloride (0.085 ml) in dry dichloromethane (2 ml) at −50° was treated with a solution of dry dimethylsulphoxide (0.165 ml) in dry dichloromethane (2 ml) over a 15 min period. Stirring was continued at −60° for 20 min and the mixture was treated with a solution of the free base of the product of Example 2 (0.22 g) in dry dichloromethane (10 ml) over a 20 min period. The mixture was stirred at −60° for 30 min and treated with triethylamine (0.4 ml). Water (10 ml) was added and the product was extracted with dichloromethane (2×20 ml). The organic solution was dried and evaporated leaving an oily residue. The residue was purified by flash column chromatography eluting with dichloromethane/methanol/ammonia (200:8:1) to give the free base of the title compound as a gum (0.11 g). A solution of the free base (0.11 g) in ethylacetate (5 ml) was treated with a solution of fumaric acid (25 mg) in a mixture of ethyl acetate (5 ml) and methanol (0.5 ml). The resulting solid was crystallised from a mixture of methanol and ethyl acetate to give the title compound as a solid (0.050 g) m.p. 184°.

T.l.c. $SiO_2$ dichloromethane/methanol ammonia 150:8:1 Rf 0.4.

EXAMPLE 6

5-[(3,4-Dichlorophenyl)acetyl]-4,5,6,7-tetrahydro-N,N-dimethylfuro[3,2-c]pyridine-4-methanamine fumarate (1:1)

(i)
4,5,6,7-Tetrahydro-N,N-dimethylfuro[3,2-c]pyridine-4-carboxamide

Following the method of Example 1 (i) intermediate 1 (0.17 g) was reacted with dimethylamine (2 ml) to give the title compound as an oil (0.095 g).

T.l.c. ($SiO_2$) Dichloromethane/methanol/ammonia (75:10:2) Rf 0.4.

(ii)
4,5,6,7-Tetrahydro-N,N-dimethylfuro[3,2-c]pyridine-4-methanamine

Following the method of Example 1(ii) the title compound was prepared as an oil (0.066 g) starting from the product of stage (i) (0.09 g).

T.l.c. ($SiO_2$) Dichloromethane/methanol/ammonia (75:8:2) Rf 0.35.

(iii)
5-[(3,4-Dichlorophenyl)acetyl]-4,5,6,7-tetrahydro-N,N-dimethylfuro[3,2-c]pyridine-4-methanamine fumarate (1:1)

Following the method of Example 1(iii) the product of stage (ii) (0.064 g) was reacted with 3,4-dichlorphenylacetic acid (0.13 g) to give the title compound as a solid (38 mg) following fumarate salt formation and crystallisation from methanol/ethylacetate m.p. 199°–200°.

EXAMPLE 7

5-[(3,4-Dichlorophenyl)acetyl]-4,5,6,7-tetrahydro-4-[(1,2,3,6-tertahydro-1-piridinyl)methyl]furo[3,2-c]pyridine fumarate (1:1)

(i) 4,5,6,7-Tetrahydrofuro[3,2-c]pyridine-4-methanol

A suspension of lithium aluminum hydride (0.6 g) in dry tetrahydrofuran (25 ml) was treated with a solution of intermediate 1 (1.8 g) in dry tetrahydrofuran (10 ml) over a 10 min period. The mixture was stirred at ambient temperature for 3 h, and water (0.6 ml) was cautiously added, followed by aqueous sodium hydroxide solution (2M; 1.8 ml) and water (0.6 ml). The mixture was filtered and the filtrate was evaporated in vacuo to give the title compound as a solid (1.15 g) m.p. 66°–9°.

(ii)
5-[(3,4-Dichlorophenyl)acetyl]-4,5,6,7-tetrahydrofuro[3,2-c]pyridine-4-methanol A solution of 3,4-dichlorophenyl acetic acid (4.6 g) in dry dichloromethane (100 ml) was treated with 1,1'-dicarbonyldiimidazole (3.6 g). The mixture was stirred at ambient temperature for 30 min. A solution of the product of stage (i) (1.13 g) in dry dichloromethane (20 ml) was added and the mixture was stirred at ambient temperature for 20 h. The mixture was washed with aqueous sodium carbonate solution (1M; 2×100 ml), dried ($Na_2SO_4$) and evaporated in vacuo. The residue was dissolved in tetrahydrofuran (50 ml) and a solution of lithium hydroxide (0.575 g) in water (40 ml) was added. The mixture was vigorously stirred at ambient temperature for 80 min. The organic solvent was removed in vacuo and the aqueous residue was extracted with dichloromethane (50 ml). The organic extract was dried ($Na_2SO_4$) and evaporated in vacuo to give a solid residue which was crystallised from methylacetate and hexane to give the title compound as a pale yellow solid (1.81 g) m.p. 155°–6°.

(iii)
5-[(3,4-Dichlorophenyl)acetyl]-4,5,6,7-tetrahydro-4-[(1,2,3,6-tetrahydro-1-piridinyl)methyl]furo[3,2-c]pyridine fumarate (1:1)

A solution of oxalyl chloride (0.16 ml) in dry dichloromethane (12 ml) at −65° was treated with a solution of dry dimethylsulphoxide (0.21 ml) in dry dichloromethane (3 ml) at −65°. The resulting solution was stirred at −65° for 20 min, a solution of the product of stage (ii) (0.40 g) in dry dichloromethane (10 ml) was added over 5 min and the mixture was stirred at −65° for 3 h. Triethylamine (1.0 ml) was added followed by water (10 ml) at −20°. The layers were separated, the aqueous layer was extracted with dichloromethane (2×10 ml) and the organic extracts were dried and evaporated to give a gum. A mixture of the gum, the tetrahydropyridine (0.2 ml) and 3 Å molecular sieves (0.5 g) in methanol (12 ml) at −65° was treated with methanolic hydrogen chloride (pH 6.5).

Sodium cyanoborohydride (183 mg) was added and the mixture allowed to warm to room temperature then stirred at room temperature for 3 days. The mixture was filtered and the filtrate evaporated. The residue was dissolved in 2N sodium carbonate solution (10 ml) and extracted with dichloromethane (3×10 ml). The dichloromethane extracts were dried and evaporated to give an oil (560 mg), which was purified by flash column chromatography using gradient elution with ether and then ether:methanol:ammonia (1000:8:1) to give the free base as an oil (89 mg).

The free base (89 mg) was dissolved in ethyl acetate (10 ml) and treated with a solution of fumaric acid (28 mg) in methanol (2 ml) to give the title compound as a powder (77 mg) m.p. 199°–200°.

Analysis: Found: C,57.4; H,4.9; N,5.20; $C_{21}H_{22}Cl_2N_2O_2 \cdot C_4H_4O_4$ requires C,57.6; H,5.0; N,5.4%.

EXAMPLE 8

5-[(4-Chlorophenoxy)acetyl]-4,5,6,7-tetrahydro-4-[(3-hydroxy-1-pyrrolidinyl)methyl]furo[3,2-c]pyridine A solution of 1,1'-carbonyldiimidazole (273 mg) and p-chlorophenoxyacetic acid (317 mg) in dry dichloromethane (12 ml) was stirred under nitrogen for 1 h at room temperature. A solution of the product of Example 2 stage (ii) (141 mg) in dichloromethane (15 ml) was added and the mixture was stirred for 18 h. The reaction mixture was washed with 2N sodium carbonate solution (2×5 ml), dried and evaporated to give a gum. A solution of the gum in a mixture of tetrahydrofuran (8 ml) and water (2 ml) was treated with lithium hydroxide (53 mg) and the mixture was stirred at room temperature for 1 h. The organic solvent was evaporated in vacuo and the aqueous residue was extracted with dichloromethane (2×10 ml). The organic extracts were dried and evaporated in vacuo to give a gum, which was purified by flash column chromatography eluting with dichloromethane:methanol:ammonia (180:8:1) to give the title compound as a foam (179 mg) m.p. 43°–45°.

Analysis: Found: C,60.05; H,5.7; N,6.85. $C_{20}H_{23}ClN_2O_4.0.5H_2O$ requires C,60.1; H,6.05; N,7.0%.

Water analysis: Found 2.25% $H_2O$ w/w≡0.5 mol %.

EXAMPLE 9

4,5,6,7-Tetrahydro-4-[(3-hydroxy-1-pyrrolidinyl)methyl]-5-[[4-(trifluoromethyl)phenyl]acetyl]furo[3,2-c]pyridine Following the method of Example 8 and using equivalent quantities of the appropriate starting materials the title compound was prepared as a form (203 mg) after purification by flash column chromatography eluting with dichloromethane:methanol:ammonia (130:8:1).

Analysis: Found: C,61.2; H,5.6; N,6.60. $C_{21}H_{23}N_2F_3O_3.0.2\ H_2O$ requires C,61.2; H,5.7; N,6.8.

T.l.c. $SiO_2$ Dichloromethane:methanol:ammonia (130:8:1) Rf 0.15.

Water analysis: Found 0.92% $H_2O$ w/w≡0.2 mol %.

EXAMPLE 10

4,5,6,7-Tetrahydro-4-[(3-hydroxy-1-pyrrolidinyl)methyl]-5-(1-naphthalenylacetyl)furo[3,2-c]pyridine Following the method of Example 8 the title compound was prepared as a foam (154 mg) from 1-naphthylacetic acid (316 mg) and 1-[(4,5,6,7-tetrahydrofuro[3,2-c]pyridin-4-yl]methyl]-3-pyrrolidinol (141 mg) m.p. 62°–68°.

Analysis: Found: C,72.3; H,6.7; N,6.8. $C_{24}H_{26}N_2O_3.0.4\ H_2O$ requires C,72.5; H,6.8; N,7.05.

EXAMPLE 11

5-[(3,4-Dichlorophenyl)acetyl]-4,5,6,7-tetrahydro-4-[(3-hydroxy-1-pyrrolidinyl)methyl]-2-methylfuro[3,2-c]pyridine (i) Methyl 4,5,6,7-tetrahydro-2-methylfuro[3,2-c]pyridine-4-carboxylate hydrochloride A solution of the 5-methyl-2-furanethanamine (1.3 g) in dry diethyl ether (50 ml) was treated with ethereal hydrogen chloride and the resulting solid was dried in vacuo. A suspension of the solid in dry acetonitrile (60 ml) was treated with freshly distilled methyl glyoxylate (2.6 g) and the mixture was stirred for 20 min. The solution was evaporated in vacuo and the residue was crystallised from ethylacetate (30 ml) to give the title compound as a powder (1.15 g) m.p. 152°–4°.

(ii) 1-[(4,5,6,7-Tetrahydro-2-methylfuro[3,2-c]pyridin-4-yl)carbonyl]-3-pyrrolidinol A solution of the product of stage (i) (0.6 g) was basified with potassium carbonate solution (1 g, in 10 ml $H_2O$), and the free base was extracted into dichloromethane (3×10 ml). The combined extracts were dried and evaporated to give an oil (495 mg). A mixture of the oil (0.43 g) and 3-pyrrolidinol (0.9 g) was heated at 120° for 1 h. The excess reagent was removed by distillation (b.p. 125°, ~8 mmHg) and the residue (1.13 g) was purified by flash column chromatography eluting with dichloromethane:methanol:ammonia, (75:10:2) to give the title compound as a foam (287 mg).

Analysis: Found: C,62.4; H,7.4; N,11.1; $C_{13}H_{18}N_2O_3$ requires: C,62.4; H,7.25; N,11.2%.

(iii) 1-[(4,5,6,7-Tetrahydro-2-methylfuro[3,2-c]pyridin-4-yl)methyl]-3-pyrrolidinol A suspension of lithium aluminium hydride (110 mg) in dry tetrahydrofuran (20 ml) was treated with a solution of the product of stage (ii) (277 mg) in dry tetrahydrofuran (15 ml). The mixture was heated at 45° for 4 h. Water (0.11 ml) was cautiously added to the cooled mixture followed by aqueous sodium hydroxide (2M, 0.33 ml) and water (0.11 ml). The mixture was filtered and the filtrate was evaporated in vacuo, to give the title compound as a gum (233 mg). T.l.c. $SiO_2$ Dichloromethane:methanol:ammonia (75:10:2), Rf 0.32.

(iv) 5-[(3,4-Dichlorophenyl)acetyl]-4,5,6,7-tetrahydro-4-[(3-hydroxy-1-pyrrolidinyl)methyl]-2-methylfuro[3,2-c]pyridine To a solution of 1,1'-carbonyldiimidazole (197 mg) in dry dichloromethane (8 ml) was added 3,4-dichlorophenylacetic acid (249 mg) in dry dichloromethane (2 ml), and the resulting solution was stirred under nitrogen for 1 h, at room temperature. A solution of the product of stage (iii) (115 mg) in dichloromethane (8 ml) was added and the mixture was stirred for 3 days. The reaction mixture was washed with sodium carbonate solution (2N, 2×5 ml), dried and evaporated to give a gum. A solution of the gum in a mixture of tetrahydrofuran (8 ml) and water (2 ml) was treated with lithium hydroxide (42 mg) and the mixture was stirred at room temperature for 0.5 h. The organic solvent was evaporated in vacuo and the aqueous residue was extracted with dichloromethane (2×10 ml). The organic extracts were dried and evaporated in vacuo to give a gum (233 mg) which was purified by flash column chromatography eluting with dichloromethane:methanol:ammonia (150:8:1) to give the title compound as a foam (146 mg).

Analysis: Found: C,58.8; H,5.8; N,6.3. $C_{21}H_{24}N_2Cl_2O_3.0.18H_2O$ requires C,59.1; H,5.7; N,6.6%.

T.l.c. $SiO_2$ Dichloromethane:methanol:ammonia (150:8:1) Rf 0.15.

Water assay found 0.75% $H_2O$≡0.17 moles.

EXAMPLE 12

[S-(R*S*)]-(−)-5-[(3,4-Dichlorophenyl)acetyl]-4,5,6,7-tetrahydro-4[(3-hydroxy-1-pyrrolidinyl)methyl]-furo[3,2-c]pyridine mixture with [S-(R*S*)] isomer (1:1)

Method 1

(i)

S-(−)-3-(Acetyloxy)-1-(phenylmethyl)-2,5-pyrrolidinedione

A mixture of acetyl chloride (20 ml) and L-malic acid (6.7 g) was heated under reflux for 2 h. The solvent was removed in vacuo, and the residue was diluted with dichloromethane (100 ml). Benzylamine (20 ml) was added and the mixture was stirred at ambient temperature for 20 h. Acetyl chloride (20 ml) was added, and the mixture was heated under reflux for 5 h. The solvent was removed in vacuo and the solid residue was purified by dry flash column chromatography (eluting with ethyl acetate hexane 1:3 to give the title compound as a solid (11.5 g).

M.p. 58°-60°. $[\alpha]_D^{20}$ −40.61° [1% w/v methanol).

(ii) S-(−)-1-(Phenylmethyl)-3-pyrrolidinol

To a suspension of lithium aluminium hydride (2.45 g) in dry tetrahydrofuran (50 ml), was added a solution of the product of stage (i) (5.05 g) in dry tetrahydrofuran (50 ml) so as to maintain a gentle reflux. The mixture was stirred at ambient temperature for 3 h and heated at reflux for 1 h. The cooled reaction mixture was cautiously treated with water (2.4 ml) followed by aqueous sodium hydroxide (2M; 7.5 ml) and water (2.5 ml). The mixture was filtered and the filtrate was evaporated in vacuo to give an oily residue (4.5 g) which was purified by flash column chromatography eluting with dichloromethane:methanol:ammonia (150:8:1) to give the title compound as an oil (2.8 g).

T.l.c. SiO$_2$ Dichloromethane:methanol:ammonia (150:8:1). Rf. 0.25.

(iii) S-(−)-3-Pyrrolidinol

A solution of the product of stage (ii) (2.65 g) in a mixture of ethanol (30 ml) and acetic acid (1 ml) was hydrogenated over 10% palladium on carbon (0.5 g). The solvent was removed in vacuo and the residue was dissolved in a solution of potassium hydroxide (1 g) in ethanol (20 ml). The solvent was removed in vacuo, and the residue was extracted with dichloromethane (2×50 ml). The organic extract was filtered and evaporated. The residue was purified by distillation under reduced pressure, to give the title compound as an oil (1.11 g) (Kugelrohr b.p. 100° at 1.5 mm Hg).

T.l.c. SiO$_2$ Dichloromethane:methanol:ammonia (75:10:2) Rf. 0.05.

(iv)

[S-(R*S*)-(+)-1-[(4,5,6,7-Tetrahydrofuro[3,2-c]pyridin-4-yl)carbonyl]-3-pyrrolidinol mixture with [S(R*R*)] isomer (1:1)

A mixture of Intermediate 1 (0.5 g) and the product of stage (iii) (1 g) was heated at 120° for 1 h. The excess pyrrolidinol was removed in vacuo and the residue was purified by flash column chromatography eluting with dichloromethane:methanol:ammonia (100:10:1) to give the title compound as a foam (0.442 g). T.l.c. SiO$_2$ Dichloromethane:methanol:ammonia (75:10:2). Rf. 0.5.

(v)

[S(R*S*)]-1-[(4,5,6,7-Tetrahydrofuro[3,2-c]pyridin-4-yl)methyl]-3-pyrrolidinol mixture with [S(R*R*)] isomer (1:1)

A suspension of lithium aluminium hydride (0.135 g) in dry tetrahydrofuran (20 ml) was treated with a solution of the product of stage (iv) (0.41 g) in dry tetrahydrofuran (10 ml) over a 10 min period. The mixture was stirred at ambient temperature for 1 h and then at 40° for 2 h. Water (0.13 ml) was cautiously added, followed by aqueous sodium hydroxide (2M; 0.4 ml) and water (0.13 ml). The mixture was filtered and the filtrate was evaporated in vacuo to give the title compound as an oil (0.39 g).

T.l.c. SiO$_2$ Dichloromethane/methanol/ammonia (75:10:2).
Rf. 0.2.

(vi)

[S-(R*S*)]-(−)5-[(3,4-Dichlorophenyl)acetyl]-4,5,6,7-tetrahydro-4[(3-hydroxy-1-pyrrolidinyl)methyl]-furo[3,2-c]pyridine mixture with [S-(R*R*)]-isomer (1:1)

A mixture of 3,4-dichlorophenylacetic acid (0.44 g) and 1,1'-carbonyldiimidazole (0.35 g) in dry dichloromethane (10 ml) was stirred for 1 h at ambient temperature. The above solution was added dropwise to a solution of the product of stage (v) (0.39 g) in dry dichloromethane (20 ml) at 0°-5° over a 5 min period. The mixture was stirred at ambient temperature for 18 h, and poured into aqueous sodium carbonate solution (1M; 25 ml). The product was extracted with dichloromethane (25 ml) and the organic extract was dried and evaporated in vacuo. The residue (0.8 g) was purified by flash column chromatography eluting with dichloromethane:methanol:ammonia (150:8:1) to give the free base of the title compound as a gum (0.5 g). A solution of the free base in dry diethylether (25 ml) was treated with ethereal hydrochloride and the resulting solid was filtered off to give the title compound as a solid. (0.4 g) M.p. 184°-187°.

Assay: Found: C, 53.11; H, 5.22; N, 6.03.
$C_{20}H_{22}Cl_2N_2O_3 \cdot HCl \cdot O.3H_2O$ requires C, 53.19; H, 5.27; N, 6.20%.

$[\alpha]_D^{20}$ −1.89° (0.5%; w/v methanol).

Water Assay found 1.27% w/v $H_2O \equiv 0.3$ mole.

Method 2

A solution of oxalyl chloride (0.48 ml) in dry dichloromethane (36 ml) at −65° was treated with a solution of dry dimethylsulphoxide (0.63 ml) in dry dichloromethane (9 ml) at −65°. The resulting solution was stirred at −65° for 20 min, a solution of the product Example 7 stage (ii) (1.2 g) in dry dichloromethane (30 ml) was added over 5 min. and the mixture was stirred at −65° for 3 h. Triethylamine (3.0 ml) was added followed by water (30 ml) at −20°. The layers were separated, the aqueous layer was extracted with dichloromethane (2×30 ml) and the organic extracts were dried and evaporated to give a gum. A mixture of the gum, S-(−)-3-pyrrolidinol (0.53 ml) and 3 Å molecular sieves (1.5 g) in methanol (36 ml) at −65° was treated with methanolic hydrogen chloride until pH=6. Sodium cyanoborohydride (550 mg) was added and the mixture was allowed to warm to room temperature for 18 h. The mixture was filtered and the filtrate evaporated. The residue was dissolved in 2N sodium carbonate solution (30 ml) and extracted with dichloromethane (3×30 ml). The dichloromethane extracts were dried and evaporated to give an oil (1.8 g), which was purified by flash column chromatography eluting with dichloromethane:methanol:ammonia (150:8:1) to give the title compound as a solid (505 mg).

EXAMPLE 13

[R-(R*R*)]-(−)-5-[(Dichlorophenyl)acetyl]-4,5,6,7-tetrahydro-4-[(3-hydroxy-1-pyrrolidinyl)methyl]furo[3,2-c]pyridine hydrochloride mixture with [R-(R*S*)] isomer (1:1)

(i)

[R(R*R*)]-1-[(4,5,6,7-Tetrahydrofuro[3,2-c]pyridin-4-yl)methyl]-3-pyrrolidinol mixture with [R(R*S*)] isomer (1:1)

Following the method of Example 12 stages (i) to (v) the title compound was prepared as an oil (0.288 g) starting from D-malic acid, (6.7 g).

T.l.c. $SiO_2$ Dichloromethane:methanol:ammonia (75:10:2) Rf 0.3.

(ii)

[R-(R*R*)]-(−)-5-[(Dichlorophenyl)acetyl]-4,5,6,7-tetrahydro-4-[(3-hydroxy-1-pyrrolidinyl)methyl]furo[3,2-c]pyridine hydrochloride mixture with [R-(R*S*)] isomer (1:1)

A solution of 3,4-dichlorophenyl acetic acid (0.31 g) and 1,1'-carbonyldiimidazole (0.25 g) in dry dichloromethane (10 ml) was added to a solution of the product of stage (i) (0.280 g) in dry dichloromethane (20 ml). The mixture was stirred at ambient temperature for 18 h. The reaction mixture was washed with aqueous sodium carbonate solution (1M; 2×20 ml), dried and evaporated to give an oily residue. The residue was purified by flash column chromatography eluting with dichloromethane:methanol:ammonia (150:8:1) to give the free base of the title compound as a gum (0.35 g). A solution of the free base in a mixture of diethylether and methyl acetate was treated with ethereal hydrogen chloride to give the title compound as a solid (0.31 g). M.p. 185°–9°.

Assay: Found: C, 53.60; H, 5.00; N, 6.01.

$C_{20}H_{22}Cl_2N_2O_3 \cdot HCl$ requires C, 53.89; H, 5.20; N, 6.28%.

$[\alpha]_D^{20}$ −0.73° (0.5% w/v methanol).

EXAMPLE 14

5-[(3,4-Dichlorophenyl)acetyl]-4,5,6,7-tetrahydro-4-(1-pyrrolidinyl methyl)thieno[3,2-c]pyridine fumarate (1:1)

(i) Methyl 4,5,6,7-tetrahydrothieno[3,2-c]pyridine-4-carboxylate

A solution of 2-thiophenethanamine (0.9 g) in dry diethyl ether (10 ml) was treated with ethereal hydrogen chloride. The solvent was removed in vacuo and the solid residue was dissolved in dry acetonitrile (30 ml). Redistilled methyl glyoxaldehyde (1.2 g) was added and the mixture was stirred at ambient temperature for 3 days. The solvent was removed in vacuo and the residue was dissolved in water (30 ml) and washed with diethyl ether (2×50 ml). The aqueous solution was basified with anhydrous potassium carbonate and the product was extracted with dichloromethane (2×50 ml). The organic extract was dried and evaporated and the residue (0.9 g) was purified by flash column chromatography eluting with dichloromethane:methanol:ammonia 200:8:1 to give the title compound as an oil (0.775 g).

T.l.c. $SiO_2$; dichloromethane:methanol:ammonia (150:8:1) Rf 0.5

(ii)

1-[(4,5,6,7-Tetrahydrothieno[3,2-c]pyridin-4-yl)carbonyl] pyrrolidine

Following the method of Example 1 stage (i) the product of stage (i) (0.75 g) and pyrrolidine (1.6 ml) were reacted to give the title compound as a solid (0.6 g), m.p. 114°–116°.

(iii)

4,5,6,7-Tetrahydro-4-(1-pyrrolidinylmethyl)thieno[3,2-c] pyridine

Following the method of Example 1 stage (ii) the title compound was prepared as an oil (0.475 g) from the product of stage (ii) (0.60 g).

T.l.c $SiO_2$ Dichloromethane/methanol/ammonia (75:10:2) Rf 0.25.

(iv)

5-[(3,4-Dichlorophenyl)acetyl]-4,5,6,7-tetrahydro-4-(1-pyrrolidinylmethyl)thieno[3,2-c]pyridine fumarate (1:1)

The free base of title compound was prepared as a gum (0.51 g) from 3,4-dichlorophenylacetic acid (0.66 g) and the product of stage (iii) according to the method of Example 1 stage (iii).

A solution of the free base (0.15 g, 0.36 mmol) was dissolved in ethyl acetate (10 ml) and treated with a solution of fumaric acid (0.045 g) in a mixture of ethyl acetate and methanol. The solid was crystallised from methanol and ethyl acetate to give the title compound as a solid (0.11 g) m.p. 238°.

Assay: Found: C,53.57; H,4.98; N,4.81.

$C_{20}H_{22}Cl_2N_2OS \cdot 1.5C_4H_4O_4$ requires C,53.52; H,4.84; N,4.80%.

EXAMPLE 15 a)

[S-(R*R*)]-1-[[5-[(3,4-Dichlorophenyl)acetyl]-4,5,6,7-tetrahydrofuro [3,2-c]pyridin-4-yl]methyl]-3-pyrrolidinol acetate monohydrochloride mixture with [S-(R*S*)]-isomer (1:1)

A solution of acetyl chloride (0.025 ml) in dichloromethane (1 ml) was added to a stirred solution of triethylamine (0.044 ml) and the product of Example 12 (118 mg) in dichloromethane (10 ml) and the mixture was stirred under nitrogen for 0.5 h. The mixture was washed with sodium carbonate solution (2N, 10 ml), dried and evaporated to give a gum (179 mg), which was purified by flash chromatography eluting with dichloromethane:methanol:ammonia (450:8:1) to give the free base of the title compound as an oil (101 mg). (Diastereoisomeric ratio 1:1).

The oil was dissolved in ether (4 ml), and treated with ethereal hydrogen chloride (0.5 ml) to give the title compound as a powder (83 mg) m.p. 114° softens 91°.

Analysis: Found: C,53.2; H,5.35; N,5.3;

$C_{22}H_{24}Cl_2N_2O_4 \cdot HCl \cdot 0.7H_2O$ requires: C,52.80; H,5.3; N,5.60%.

Water analysis: Found 2.48% $H_2O$ w/w≡0.7 mol %.

b)
[S-(R*R*)]-1-[[5-[(3,4-Dichlorophenyl)acetyl]-4,5,6,7-tetrahydro[3,2-c]pyridin-4-yl]methyl]-3-pyrrolidinol acetate isomer or [S-(R*S*)]

The mixture of diastereoisomers of the free base were separated by preparative h.p.l.c. on spherisorb 5μ (25 cm×20 mm) eluting with hexane:chloroform:methanol:ammonia, (1800:200:50:1) to give the title compound (Isomer I) as a gum (84 mg).
T.l.c. $SiO_2(CH_2Cl_2:MeOH:NH_3$, 450:8:1) Rf 0.35.
Hplc (isomer I 99.25% isomer II 0%).
Retention time 12.2 min.
X-ray analysis of a single crystal shows isomer I is the [S-(R*S*)]-isomer.
Isomer II ([S-(R*R*)]-) was obtained as a gum (96 mg).
T.l.c. $SiO_2$ $(CH_2Cl_2:MeOH:NH_3$, 450:8:1) Rf 0.35.
Hplc (Isomer II 98.34% Isomer I 0.94%).
Retention time 13.6 min.

EXAMPLE 16

[R-(R*R*)]-1-[[5-[(3,4-Dichlorophenyl)acetyl]-4,5,6,7-tetrahydrofuro[3,2-c]pyridin-4-yl]methyl]-3-pyrrolidinol acetate (ester) monohydrochloride mixture with [R-(R*S*)]-isomer (1:1)

Following the method of Example 15(a) the title compound was prepared as a powder (132 mg) from the product of Example 13 m.p 114° softens 91°.
Analysis: Found: C,53.05; H,5.3; N,5.6;
$C_{22}H_{24}Cl_2N_2O_4.HCl.O.7H_2O$ requires: C,52.80; H,5.3; N,5.60%
Water analysis: Found: 2.52% $H_2O$ w/w≡0.7 mol %

EXAMPLE 17

[S-(R*R*)]-5-[(3,4-Dichlorophenyl)acetyl]-4,5,6,7-tetrahydro-4[(3-hydroxy-1-pyrrolidinyl)methyl]furo[3,2-c]pyridine isomer A solution of the product of Example 15(b) ([S-(R*R*)]-isomer) (138 mg) in tetrahydrofuran (10 ml) was treated with a solution of lithium hydroxide (22 mg) in water (2 ml) and the mixture was stirred at room temperature for 18 h. The organic solvent was removed in vacuo, the aqueous residue was extracted with dichloromethane (2×10 ml) and the combined extracts were dried and evaporated to give the title compound as a foam (90 mg) m.p. 42°-45° (softens 27°).
Analysis: Found: C,57.9; H,5.6; N,6.3.
$C_{20}H_{22}Cl_2N_2O_3.O.3H_2O$ requires C,57.9; H,5.5; N,6.8%.
Water analysis: Found: 1.31% $H_2O$ w/w=0.3 mol %.

The following examples illustrate pharmaceutical formulations containing [S-(R*R*)]-5-[(3,4-dichlorophenyl)acetyl]-4,5,6,7-tetrahydro-4-[(3-hydroxy-1-pyrrolidinyl)methyl]furo[3,2-c]pyridine. Other compounds of the invention may be formulated in a similar manner.

| TABLETS FOR ORAL ADMINISTRATION DIRECT COMPRESSION | |
|---|---|
| | mg/tablet |
| Active ingredient | 20 |
| Calcium Hydrogen Phosphate B.P.* | 75.5 |
| Croscarmellose sodium USP | 4 |
| Magnesium Stearate, B.P. | 0.5 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| INJECTION FOR INTRAVENOUS ADMINISTRATION | |
|---|---|
| | mg/ml |
| Active ingredient | 5 |
| Sodium Chloride BP | as required |
| Water for Injection BP 0.5 to 2 ml | |
| INTRAVENOUS INFUSION | |
| Dextrose 5% aqueous solution BP | 10-100 ml |
| Active ingredient | 700 mg |
| Sodium Chloride BP | as required |

For infusion at a rate of 700 mg per hour.

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A compound having a formula:

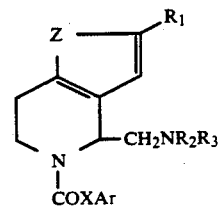

wherein
$R_1$ represents hydrogen; unsubstituted $C_{1-6}$alkyl; $C_{1-6}$alkyl substituted by hydroxy; halogen; —$COR_4$ or —$CO_2R_4$ (where $R_4$ represents hydrogen or unsubstituted $C_{1-6}$alkyl or $C_{1-6}$alkyl substituted by hydroxy);

—$NR_2R_3$ forms a 5-membered (optionally containing an oxygen atom adjacent to the nitrogen) or a 6-membered ring, which ring optionally contains one unit of unsaturation and which is substituted by hydroxy, $C_{1-6}$acyloxy, oxo, methylidine optionally substituted by nitrile, phenyl, carboxyl, amido, $C_{1-6}$alkyl, phenethyl, hydroxymethyl, methoxycarbonylethyl or aminocarbonylethyl groups, —$COR_5$ (where $R_5$ represents $C_{1-6}$alkyl, $OR_6$ or —$NHR_6$, and $R_6$ represents hydrogen, $C_{1-6}$alkyl, aryl or ar($C_{1-6}$)alkyl) or said ring is substituted by=$NOR_7$ (where $R_7$ represents $C_{1-6}$alkyl);

Z represents —O—;

X represents a direct bond, —$CH_2$— or —$CH_2O$—;

Ar represents naphthyl or phenyl substituted by one or more halogen, $CF_3$ or $NO_2$ groups; and pharmaceutically acceptable salts thereof.

2. A compound according to claim 1 having the stereoisomeric form represented by formula (Ia)

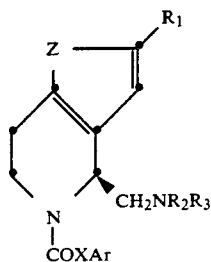

3. A compound according to claim 1 wherein $R_1$ represents H, CHO, $CH_2OH$ or $CH_3$.

4. A compound according to claim 1 wherein $NR_2R_3$ represents substituted pyrrolidine or tetrahydropyridine.

5. A compound according to claim 1 wherein X represents —$CH_2$— and Ar represents halosubstituted phenyl.

6. A compound selected from the group consisting of
5-[(3,4-Dichlorophenyl)acetyl]-4,5,6,7-tetrahydro-4-[(3-hydroxy-1-pyrrolidinyl)methyl]furo[3,2-c]pyridine;
5-[(3,4-Dichlorophenyl)acetyl]-4,5,6,7-tetrahydro-4-[(3-oxo-1-pyrrolidinyl)methyl]furo[3,2-c]pyridine;
5-[(3,4-Dichlorophenyl)acetyl]-4,5,6,7-tetrahydro-4-[(3-hydroxy-1-pyrrolidinyl)methyl]-2-methylfuro[3,2-c]pyridine;
4,5,6,7-Tetrahydro-4-[(3-hydroxy-1-pyrrolidinyl)methyl]-5-(1-naphthalenylacetyl)furo[3,2-c]pyridine;
5-[(3,4-Chlorophenoxy)acetyl]-4,5,6,7-tetrahydro-4-[(3-hydroxy-1-pyrrolidinyl)methyl]furo[3,2-c]pyridine;

and pharmaceutically acceptable salts thereof.

7. A compound according to claim 2 wherein $R_1$ represents H, CHO, $CH_2OH$ or $CH_3$.

8. A compound according to claim 2 wherein $NR_2R_3$ represents substituted pyrrolidine or tetrahydropyridine.

9. A compound according to claim 4 wherein $NR_2R_3$ represents substituted pyrrolidine or tetrahydropyridine.

10. A compound according to claim 2 wherein X represents —$CH_2$— and Ar represents halosubstituted phenyl.

11. A compound according to claim 3 wherein X represents —$CH_2$— and Ar represents halosubstituted phenyl.

12. A compound according to claim 4 wherein X represents —$CH_2$— and Ar represents halosubstituted phenyl.

13. A compound as claimed in claim 6, which is
5-[(3,4-Dichlorophenyl)acetyl]-4,5,6,7-tetrahydro-4-[(3-hydroxy-1-pyrrolidinyl)methyl]furo[3,2-c]pyridine;
or a pharmaceutically acceptable salt thereof.

14. A compound as claimed in claim 6, which is
5-[(3,4-Dichlorophenyl)acetyl]-4,5,6,7-tetrahydro-4-[(3-oxo-1-pyrrolidinyl)methyl]furo[3,2-c]pyridine;
or a pharmaceutically acceptable salt thereof.

15. A compound as claimed in claim 6, which is
5-[(3,4-Dichlorophenyl)acetyl]-4,5,6,7-tetrahydro-4-[(3-hydroxy-1-pyrrolidinyl)methyl]-2-methylfuro[3,2-c]pyridine;
or a pharmaceutically acceptable salt thereof.

16. A compound as claimed in claim 6, which is
4,5,6,7-Tetrahydro-4-[(3-hydroxy-1-pyrrolidinyl)methyl]-5-(1-naphthalenylacetyl)furo[3,2-c]pyridine;
or a pharmaceutically acceptable salt thereof.

17. A compound as claimed in claim 6, which is
5-[(3,4-Chlorophenoxy)acetyl]-4,5,6,7-tetrahydro-4-[(3-hydroxy-1-pyrrolidinyl)methyl]furo[3,2-c]pyridine;
or a pharmaceutically acceptable salt thereof.

18. A pharmaceutical composition which comprises an effective amount of a compound of formula (I) as defined in claim 1 or a pharmaceutically acceptable salt together with a pharmaceutically acceptable carrier therefor.

19. A method of treating a human suffering from pain or cerebral ischaemia which comprises administering to the patient an effective amount of a compound of formula (I) as defined in claim 1 or a physiologically acceptable salt thereof.

* * * * *